United States Patent [19]

Bacon

[11] Patent Number: 5,141,931
[45] Date of Patent: Aug. 25, 1992

[54] 5-QUINOLINYLPYRIDINONES, CARDIOTONIC COMPOSITIONS AND METHODS

[75] Inventor: Edward R. Bacon, East Greenbush

[73] Assignee: Sterling Winthrop Inc., New York, N.Y.

[21] Appl. No.: 637,109

[22] Filed: Jan. 3, 1991

[51] Int. Cl.$^5$ .................. A01N 55/02; C07D 401/04
[52] U.S. Cl. .................................. 514/187; 546/167
[58] Field of Search .................... 546/167; 514/187

[56] References Cited

U.S. PATENT DOCUMENTS

| | | | |
|---|---|---|---|
| 4,313,951 | 2/1982 | Lesher et al. | 424/263 |
| 4,517,192 | 5/1985 | Lesher | 514/345 |
| 4,559,352 | 12/1985 | Lesher et al. | 514/344 |
| 4,595,762 | 6/1986 | Lesher et al. | 546/288 |
| 4,710,507 | 12/1987 | Campbell | 514/312 |
| 4,785,005 | 11/1988 | Campbell et al. | 514/312 |

FOREIGN PATENT DOCUMENTS 8400756  3/1984  PCT Int'l Appl.

OTHER PUBLICATIONS

*Chemical Abstracts*, vol. 109 No. 11, #92799n, 1987, Gil et al., "Preparation of pyridinone derivatives as cordiotonic agents".

Echavarren and Stille, "Palladium-Catalyzed Coupling of Aryl Triflates with Organostannanes", J. Am. Chem. Soc. 109:5478-5486 (1987).

*Primary Examiner*—C. Warren Ivy
*Assistant Examiner*—Raymond Covington
*Attorney, Agent, or Firm*—Philip E. Hansen; Paul E. Dupont

[57] ABSTRACT

6-Alkyl-5-(6, or 7-quinolinyl)-3-(substituted)-2(1H)-pyridinones useful as cardiotonics are synthesized by reaction of trialkylquinolinylstannanes with 6-alky-5-halo-3-(substituted)-2(1H)-pyridinones. Compositions containing these pyridinones and methods of using them to treat congestive heart failure are provided.

10 Claims, No Drawings

5-QUINOLINYLPYRIDINONES, CARDIOTONIC COMPOSITIONS AND METHODS

BACKGROUND OF THE INVENTION

1. Field of the Invention

The Invention relates to 5-(6-quinolinyl)-and 5-(7-quinolinyl)-2(1H)-pyridinones, their cardiotonic use, their preparation and intermediates in their synthesis.

2. Information Disclosure Statement

Campbell et al. PCT application WO 84/00756 discloses as cardiotonics 1,2-dihydro-2-oxo-5-(4-quinolinyl)-3-pyridinecarbonitrile; 3-bromo-5-(4-quinolinyl)-2(1H)-pyridinone; 1,2-dihydro-2-oxo-5-(4-quinolinyl)-2(1H)-pyridinone; 1,2-dihydro-2-oxo-5-(2-quinolinyl)-3-pyridinecarbonitrile; and 6-methyl-5-(2-quinolinyl)-2(1H)-pyridinone.

Campbell et al. U.S. Pat. No. 4,785,005 discloses as a cardiotonic 6-[3-cyano-6-methyl-2-oxo-(1H)-pyridin-5-yl]-1,2,3,4-tetrahydro-2-oxoquinoline.

Campbell and Roberts U.S. Pat. No. 4,710,507 discloses as a cardiotonic 2-methoxy-6-(2-methyl-pyridinyl)quinoline.

Echavarren and Stille [*J. Am. Chem. Soc.* 109, 5478-5486] disclose, without an indication of utility, 8-quinolinylmethylstannane.

SUMMARY OF THE INVENTION

In a composition of matter aspect, the invention pertains to a compound of formula I or a salt thereof

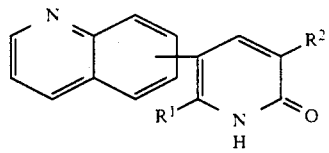

wherein $R^1$ is methyl or ethyl, preferably methyl; $R^2$ is cyano, bromo, amino or methyl, preferably cyano; and the pyridinone ring is joined to the quinoline ring at the 6- or 7- position of the quinoline. The compounds have utility as cardiotonic for preparing a compound of formula Ia

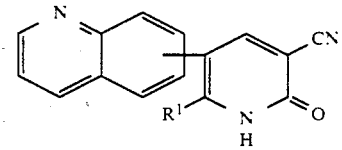

which comprises reacting a tri-lower-alkyl 6- or 7-quinolinylstannane with a 3-cyano-5-halo-6-$R_1$-2(1H)pyridinone. Halo or halogen for the purposes of the present invention means chlorine, bromine or iodine.

In a method aspect the present invention relates to a method for increasing cardiac contractility in a patient which comprises administering a compound of formula I.

In a further composition of matter aspect, the invention relates to compounds of formula IIa

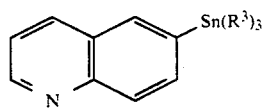

wherein $R^3$ is lower-alkyl. Lower-alkyl, for the purposes of the present invention, means alkyl having four or fewer carbon atoms in straight or branched chains. Said compounds are useful as intermediates in the synthesis of the cardiotonic compounds of formula I.

In another composition aspect the invention relates to pharmaceutical compositions for increasing cardiac contractility comprising a pharmaceutically acceptable carrier and a compound of formula I or a pharmaceutically acceptable salt thereof

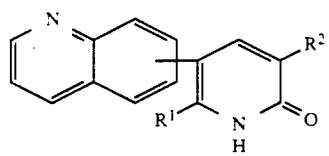

wherein $R^1$ and $R^2$ are as defined before. Throughout the following description the variables retain the definitions initially assigned to them.

DETAILED DESCRIPTION INCLUSIVE OF PREFERRED EMBODIMENTS

The synthesis of compounds of the invention may be outlined as shown

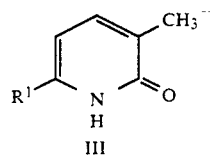
III

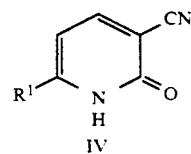
IV

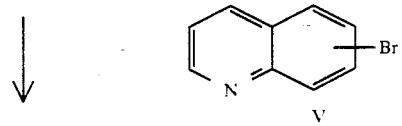
V

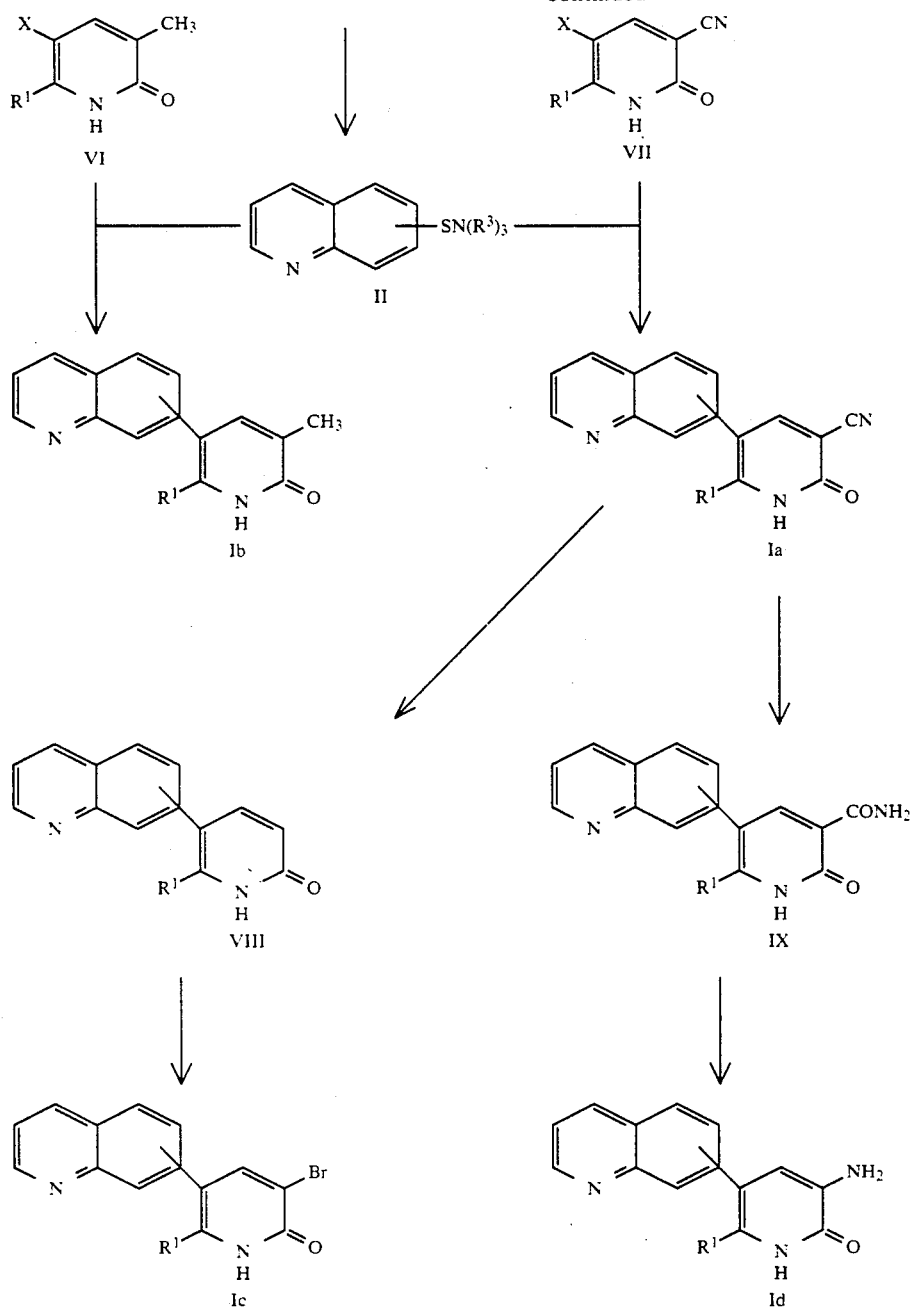

wherein X is Cl, Br or I.

A 3,6-dialkyl-2(1H)-pyridinone of formula III available by the method of Errara [*Chemische Berichte* 34, 3696 (1901)] is halogenated to produce a 5-halo-3,6-dialkyl-2(1H)-pyridinone of formula VI. In the case where X is bromine this is conveniently accomplished by treatment of a solution of the pyridinone (III) and two equivalents of sodium acetate in acetic acid with one equivalent of bromine at room temperature. In the case where X is iodine, the conversion is accomplished by treatment of a solution of the pyridinone (III) and one equivalent of N-iodosuccinimide in acetic acid with a catalytic amount of trifluoroacetic acid.

The 5-halo-3,6-dialkyl-2(1H)-pyridinone (VI) is combined with about 1.1 equivalents of a 6- or 7-quinolinyltrialkylstannane, preferably a tributyl stannane, and a catalytic amount of bis(triphenylphosphine)palladium (II) chloride in a suitable solvent, preferably dimethylformamide, and heated at 60–150° C. to produce a 6-alkyl-3-methyl-5-(6- or 7-quinolinyl)-2(1H)-pyridinone (Ib).

When it is desired that $R^2$ be other than methyl, i.e. $NH_2$, CN or Br, a 6-alkyl-1,2-dihydro-2-oxo-3-pyridinecarbonitrile of formula IV is reacted as described above with either bromine or N-iodosuccinimide to produce the corresponding 5-halo compound (VII). The 5-halopyridinone VII is reacted with a quinolinyl trialkylstannane and a palladium catalyst as before to produce a 6-alkyl-1,2-dihydro-2-oxo-5-(quinolinyl)-3-pyridinecarbonitrile (Ia). The nitrile (Ia) may then be converted to the corresponding 3-bromopyridinone (Ic) by hydrolysis and decarboxylation in refluxing 85% phosphoric acid by the procedure described in U.S. Pat. No. 4,517,192 which is incorporated herein by reference (vide example B-5), followed by bromination with bromine in acetic acid according to the procedure of U.S. Pat. No. 4,313,951 which is incorporated herein by reference (vide examples F-1 and F-2). Alternatively, the nitrile (Ia) may be converted to the amine (Id) by hydrolysis in cold, concentrated sulfuric acid to the amide (IX) according to the procedure described in U.S. Pat. No. 4,595,762 which is incorporated herein by reference (vide example C-3), followed by Hoffman rearrangement of the amide with sodium hypobromite according to the procedure described in U.S Pat. No. 4,559,352 which is incorporated herein by reference (vide example C-1).

The 6-alkyl-1,2-dihydro-2-oxo-3-pyridinecarbonitriles, which are the starting materials for the synthesis of compounds Ia, Ic and Id, are available commercially or can be prepared by procedures known in the art (vide U.S. Pat. No. 4,451,469).

The quinolinyltrialkylstannanes (II) which are starting materials for the compounds of the invention may be prepared from the corresponding 6- or 7-bromoquinolines by lithiation with 1.3 equivalents of n-butyllithium in an inert solvent, preferably THF, at $-100°$ to $-50°$ followed by displacement of the lithium with trialkyltin chloride, preferably tributyltin chloride, at $-100$ to $-30°$. It is preferred that the resulting quinolinyltrialkystannane (II) be purified to obtain better yields in the coupling with 5-halopyridinones. This is accomplished by chromatography on silica gel eluting with 30% ether in hexane.

The bromoquinolines (V) are available by the method of O'Murcha [*Synthesis* 1989, 880] or Butler and Gordon [*J. Het. Chem.* 12, 1015-1020 (1975)].

The compounds of formula I are useful both in the free base form and the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention, it may be found convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The structures of the compounds of the invention were established by the mode of synthesis, by elemental analysis, mass spectroscopy and by infrared, ultraviolet, and nuclear magnetic resonance spectroscopy. The course of the reactions and the identity and homogeneity of the products were assessed by thin layer chromatography (TLC).

In the following procedures, melting points are given in degrees C and are uncorrected. The abbreviation THF stands for tetrahydrofuran and DMF stands for N,N-dimethylformamide.

EXAMPLE 1

6-Quinolinyltributylstannane

To 250 mL of THF was added 14 g (67 mmol) of 6-bromoquinoline and 44 mL (88 mmol) of 2M butyllithium in pentane was added at $-70°$ under argon. The reaction was stirred for 15 minutes and 28.4 g (87.2 mmol) of tributyltin chloride was added at such a rate that the temperature remained below $-60°$. When addition was complete, the mixture was allowed to warm to $-50°$ at which point the dark orange color characteristic of the anion became light amber. The mixture was stirred for 14 hrs at $-70°$ and poured into ice-water and ether. The layers were separated, the ether layer washed with water, dried with magnesium sulfate, filtered and concentrated. The resultant oil was chromatographed on a silica gel column (30 cm × 6 cm) using 30% ether in hexane to provide 17.8 g (63%) of 6-quinolinyltributylstannane.

EXAMPLE 2

1,2-Dihydro-5-iodo-6-methyl-2-oxo-3-pyridinenitrile

A mixture of 13.4 g (0.1 mole) of 1,2-dihydro-6-methyl-2-oxo-3-pyridinecarbonitrile, 22.5 g (0.1 mole) of N-iodosuccinimide and 5 mL of trifluoroacetic acid in 250 mL of acetic acid was heated to reflux under argon for 4 hrs. The reaction was cooled and filtered to remove the crystalline precipitated product which was washed with water and ether and air dried to give 22.3 g (86%) of the 5-iodopyridinone as dense, light yellow needles, mp 260-264.

EXAMPLE 3

1,2-Dihydro-6-methyl-2-oxo-5-(6-quinolinyl)-3-pyridinecarbonitrile

A solution of 44.8 g (0.107 mole) of 6-quinolinyltributylstannane of Example 1, 25.3 g (0.097 mole) of 1,2-dihydro-5-iodo-6-methyl-2-oxo-3-pyridinenitrile of Example 2 and 2.04 g (2.9 mmol) of bis(triphenylphosphine)palladium (II)chloride in 125 mL of DMF was heated at 145° for 3 hrs under nitrogen. The reaction was allowed to cool to about 60° and filtered through a pad of diatomaceous earth. The filtrate was poured into 3.8 L of anhydrous ether, stirred at room temperature for 10 minutes, and then at 0° for 40 minutes. The product was filtered off and rinsed with cold ether. The resulting 22 g of gray solid, after drying in air, was slurried in 2.5 L of 0.5 N HCl for 10 minutes and the solution was filtered to remove any insoluble residue. The filtrate was treated with concentrated ammonia to pH 9 and stirred at 0° for 40 minutes. The resulting precipitate was filtered, washed with cold water and dried to yield 12.9 g of product. The product was recrystallized from 100 mL of DMF and the recrystallized a second time from 750 mL of 5% methanol in chloroform to yield 6.14 g (24%) of product, mp 288–290°.

The methanesulfonate salt was prepared by treating 3 g (11.5 mmol) of the quinolinylpyridinone with 1.5 mL (23 mmol) of methanesulfonic acid in 600 mL of hot ethanol. There was obtained 3.81 g of the methanesulfonate salt which melted above 300° with decomposition.

The hydrochloride salt of the product was prepared by treating 3.1 g (11.9 mmol) of the quinolinylpyridinone with 50 mL of saturated ethanolic HCl in 600 mL of hot ethanol. Upon cooling, 3.46 g of the hydrochloride was obtained, mp >286°.

EXAMPLE 4

7-Quinolinyltributylstannane

By a procedure substantially similar to that of Example 1, it is contemplated that 7-quinolinyltributylstannane may be obtained from 7-bromoquinoline and tributyltin chloride.

EXAMPLE 5

6-Ethyl-1,2-dihydro-5-iodo-2-oxo-3-pyridinecarbonitrile

By a procedure substantially similar to that of Example 2, it is contemplated that 6-ethyl-1,2-dihydro-5-iodo-2-oxo-3-pyridinecarbonitrile may be obtained from 6-ethyl-1,2-dihydro-2-oxo-3-pyridinecarbonitrile and N-iodosuccinimide.

EXAMPLE 6

6-Ethyl-1,2-dihydro-2-oxo-5-(7quinolinyl)-3-pyridinecarbonitrile

By a procedure substantially similar to that of Example 3, it is contemplated that 6-ethyl-1,2-dihydro-2-oxo-5-(7-quinolinyl)-3-pyridinecarbonitrile may be obtained from 6-ethyl-1,2-dihydro-5-iodo-2-oxo-3-pyridinecarbonitrile of Example 5 and 7-quinolinyltributylstannane of Example 4.

The cardiotonic activity of the compound of Example 3 was demonstrated by the following procedures:

Procedure 1—Phosphodiesterase III Inhibition

Phosphodiesterase III (PDE III) was obtained by a slight modification of the methods of Thompson et al. [*Advances in Cyclic Nucleotide Research* vol. 10, 69–92, (1979)] and Weishaar et al. [*Biochemical Pharmacology* 35, 787–800 (1986)]. Thoracic aorta from mongrel dogs was minced with fine scissors and homogenized in 10 volumes of a buffer containing 10 mM tris acetate, pH 7.5, 2 mM magnesium chloride, 1mM dithiothreitol and 2000 units per mL of aprotinin. This and subsequent procedures were performed at 0–4°. The tissue was homogenized, the homogenate was sonicated and the resultant homogenate was centrifuged at 48,000 g for 30 minutes. The resulting supernatant fraction was applied to a diethylaminoethyl ether (DEAE) cellulose column that had been equilibrated with 35 or 70 mM sodium acetate containing 1 mM dithiothreitol at pH 6.5. After application of the sample, the column was washed with 2–3 bed volumes of the equilibration buffer and the PDE isozyme was eluted from the column using a continuous sodium acetate gradient to 1 molar. Fractions of approximately 5 mL were collected and assayed for cAMP and cGMP PDE activity at substrate concentrations of 1 $\mu$M. Appropriate fractions corresponding to peak three were pooled and dialyzed against 70 mM sodium acetate, 0.5 mM dithiothreitol for at least 20 hours. Following dialysis, the PDE III fractions were concentrated to approximately 14% of their original volume using an Amicon ultrafiltration cell system. PDE III activity was measured as described by Thompson et al. and Weishaar et al. Each assay was performed in triplicate, and the $IC_{50}$ for inhibition was calculated from a concentration response curve as described by Tallarida and Murray [*Manual of Pharmacologic Calculations with Computer Programs*, procedure 8 page 14–19, Springer-Verlag, New York, 1981].

In this system, the $IC_{50}$ of the compound of Example 3 was 57 nM; the $IC_{50}$ for milrinone, a clinically effective cardiotonic agent, was 500 nM.

Procedure 2—In vivo Vasodilation in the Rat

Normotensive male Sprague-Dawley rats of 325–425 g were anesthetized with sodium pentobarbital and an arterial catheter was placed in the abdominal aorta via the femoral artery. The catheter was tunneled subcutaneously, exteriorized at the nape of the neck, filled with heparinized saline and sealed with a stainless steel plug. The wounds were sutured and a suspension of penicillin G benzathine and penicillin G procaine was administered subcutaneously. All animals were allowed at least two days recovery prior to testing.

Rats were fasted 17 hours then placed into individual plexiglass boxes. The arterial catheter was connected to a Statham pressure transducer, positioned at the heart level, and the arterial pressure signal was recorded on a polygraph. The animals remained undisturbed for at least one hour to adapt to the testing environment. After the adaptation period, three baseline arterial pressure and heart rate measurements were taken at 15-minute intervals prior to the administration of the test drug. Rats were randomly assigned to treatment groups and received either the compound of Example 3 or vehicle (distilled water, 2 mL/kg) orally by gavage. Six to eight animals were included in each treatment group. Arterial pressure and heart rate were measured at 15-minute intervals for the first hour and 30-minute intervals for the next four hours following the administration of drugs.

The data were analyzed by one-way analysis of variance for repeated measures. All points were compared peak to baseline with Student Newman-Keuls Test of multiple means. A probability of less than 5% was considered statistically significant. The compound of Example 3 at 0.4 mg/kg showed an area under the curve for reduction of mean arterial pressure of 75% with a statistical significance at all times to the end of the test at six hours.

The compounds of the invention can be prepared for use by conventional pharmaceutical procedures: that is, by dissolving or suspending them or their pharmaceutically acceptable salts in a pharmaceutically acceptable vehicle, e.g., water, aqueous alcohol, glycol, oil solution or oil-water emulsion, for parenteral or oral administration; or by incorporating them in unit dosage form as capsules or tablets for oral administration either alone or in combination with conventional adjuvants or excipients, e.g., calcium carbonate, starch, lactose, talc, magnesium stearate, gum acacia, and the like.

The percentage of active component in the composition and method for treating or preventing arrhythmia can be varied so that a suitable dosage is obtained. The dosage administered to a particular patient is variable depending upon the clinician's judgment using as the criteria: the route of administration, the duration of treatment, the size and condition of the patient, the potency of the active component, and the patient's response thereto. An effective dosage amount of active component can thus be determined by the clinician considering all criteria and utilizing his best judgment on the patient's behalf.

I claim:

1. A compound of formula I

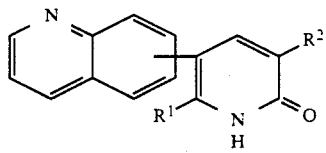

or a salt thereof, wherein $R^1$ is methyl or ethyl;

$R^2$ is cyano, bromo, amino or methyl; and the pyridinone ring is joined to the quinoline ring at the 6- or 7-position of the quinoline.

2. A compound according to claim 1 wherein said quinoline ring is joined at the 6-position.

3. A compound according to claim 2 wherein $R^2$ is cyano.

4. A compound according to claim 3 wherein $R^1$ is methyl.

5. 1,2-Dihydro-6-methyl-2-oxo-5-(6-quinolinyl)-3-pyridinecarbonitrile according to claim 4.

6. 1,2-Dihydro-6-methyl-2-oxo-5-(7-quinolinyl)-3-pyridinecarbonitrile according to claim 1.

7. A method for increasing cardiac contractility in a patient requiring such treatment which comprises administering a cardiotonically effective amount of a compound according to claim 1.

8. A method for increasing cardiac contractility in a patient requiring such treatment which comprises administering a cardiotonically effective amount of 1,2-dihydro-6-methyl-2-oxo-5-(6-quinolinyl)-3-pyridinecarbonitrile according to claim 5.

9. A composition for increasing cardiac contractility which comprises a pharmaceutically acceptable carrier and, as the active component thereof, a cardiotonically effective amount of a compound according to claim 1 or a pharmaceutically acceptable salt thereof.

10. A composition for increasing cardiac contractility which comprises a pharmaceutically acceptable carrier and, as the active component thereof, a cardiotonically effective amount of 1,2-dihydro-6-methyl-2-oxo-5-(6-quinolinyl)-3-pyridinecarbonitrile or a pharmaceutically acceptable salt thereof according to claim 5.

* * * * *

UNITED STATES PATENT AND TRADEMARK OFFICE
CERTIFICATE OF CORRECTION

PATENT NO. : 5,141,931
DATED : August 25, 1992
INVENTOR(S) : Edward R. Bacon

It is certified that error appears in the above-identified patent and that said Letters Patent is hereby corrected as shown below:

Column 1, lines 43-45 the section starting with "The compounds..." should read as follows:
-- The compounds have utility as cardiotonic agents.

In a process aspect the invention relates to a process for preparing a compound of formula Ia --.

Signed and Sealed this

Twenty-sixth Day of October, 1993

Attest:

BRUCE LEHMAN

Attesting Officer

Commissioner of Patents and Trademarks